United States Patent [19]

Hattori

[11] 4,343,300
[45] Aug. 10, 1982

[54] DATA TRANSMISSION SYSTEM FOR AN ENDOSCOPE APPARATUS

[75] Inventor: Shinichiro Hattori, Tokyo, Japan

[73] Assignee: Olympus Optical Co., Ltd., Tokyo, Japan

[21] Appl. No.: 187,538

[22] Filed: Sep. 16, 1980

[30] Foreign Application Priority Data

Sep. 20, 1979 [JP]  Japan .................................. 54-121225

[51] Int. Cl.³ ............................ A61B 1/04; A61B 1/06
[52] U.S. Cl. .......................................... 128/6; 354/62
[58] Field of Search ................. 128/6, 7, 8, 9; 354/33, 354/62, 63

[56] References Cited

U.S. PATENT DOCUMENTS

| | | | |
|---|---|---|---|
| 3,599,630 | 8/1971 | Sato et al. | 354/62 X |
| 3,726,272 | 4/1973 | Fukami et al. | 354/62 X |
| 4,153,356 | 5/1979 | Hama | 354/62 |
| 4,273,431 | 6/1981 | Farmer et al. | 354/62 X |
| 4,281,910 | 8/1981 | Takayama | 128/4 X |
| 4,310,228 | 1/1982 | Terada | 128/6 X |

Primary Examiner—Hugh R. Chamblee
Assistant Examiner—Robert P. Swiatek

[57] ABSTRACT

Data transmission/reception devices are provided in endoscope, photographic attachment and light source unit. The data transmission/reception devices are connected with one another by two-way data transmission lines.

10 Claims, 9 Drawing Figures

DATA TRANSMISSION SYSTEM FOR AN ENDOSCOPE APPARATUS

This invention relates to a data transmission system for an endoscope apparatus capable of data transmission between an endoscope, a light source unit, and a photographic attachment.

In a prior art endoscope system, operation instructions from the endoscope, such as instructions for air feed, water feed, suction, etc., are transmitted to the light source unit, and an operating member inside the light source unit operates in accordance with such operation instructions to control the air feed, water feed, suction, etc. A release signal is supplied from the photographic attachment to the light source unit, and a light source disposed in the light source unit is controlled in response to the release signal. According to such prior art endoscope system, the operation instructions are transmitted only in one direction from the endoscope and photographic attachment to the light source unit. Therefore, the endoscope can transmit only limited data, and cannot be a multifunction system.

The object of this invention is to provide a data transmission system for an endoscope apparatus capable of duplex data transmission between at least two among an endoscope, a light source unit, and a photographic attachment, thereby diversifying the function of the endoscope apparatus.

According to this invention, there is provided a data transmission system for an endoscope apparatus in which data transmission/reception devices are disposed severally in at least two of an endoscope, a light source unit, and a photographic attachment, and are coupled with one another by means of duplex channels.

This invention can be more fully understood from the following detailed description when taken in conjunction with the accompanying drawings, in which.

Figure 1:
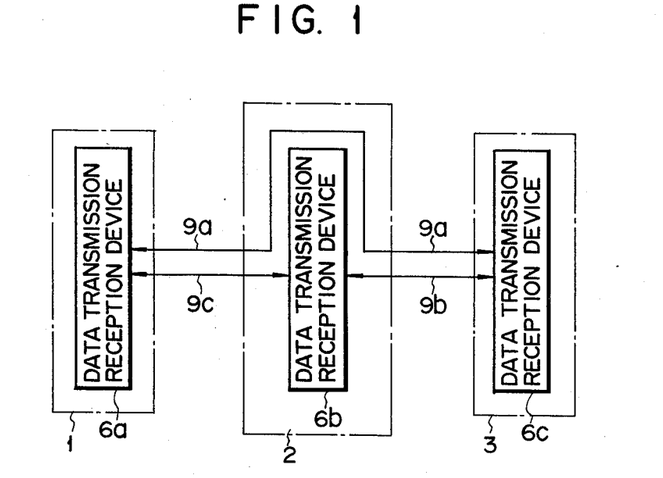
FIG. 1 is a block circuit diagram of a data transmission system for an endoscope apparatus according to an embodiment of this invention.

As shown in FIG. 1, a photograhic attachment 1, an endoscope 2, and a light source unit 3 are provided with data transmission/reception devices 6a, 6b and 6c, respectively. A two-way data transmission line 9a is provided between the respective data transmission/reception devices 6a and 6c of the photographic attachment 1 and the light source unit 3. This data transmission line 9a is a half-duplex channel formed of e.g. electric wires or optical fibers. Also, a two-way data transmission line 9b is provided between the endoscope data transmission/reception device 6b and the light source unit data transmission/reception device 6c. Moreover, a two-way data transmisson line 9c is provided between the photographic attachment data transmission/reception device 6a and the endoscope data transmission/reception device 6b. Like the data channel 9a, the data channels 9b and 9c are half-duplex channels formed of e.g. electric wires or optical fibers. The data transmission/reception devices 6a, 6b and 6c may be composed of one-chip microprocessors of USART's (universal synchronous-asynchronous receiver-transmitters).

According to the aforementioned endoscope data transmission system, operation instructions or measurement data produced at the photographic attachment 1, endoscope 2 and light source unit 3 are coverted into signals fit for data transmission by controllers formed of such elements as one-chip microprocessors that are incorporated severally in the photographic attachment, endoscope and light source unit, and are transmitted through the data transmission-reception device by means of the two-way data transmission lines between those three units, i.e. the photographic attachment, endoscope and light source unit. In such transmission, the data can be transmitted as they are in the bitparallel form if the number of bus lines in the channels is large. If the number of the bus lines is limited in relation to the number of connector pins, however, the data may some times have to be converted from parallel to serial for bit-serial transmission. In this case, the parallel-to-serial conversion is performed in accordance with the program of the microprocessor serving as the controller, and the resultant data may be delivered from an output port or a serial output terminal with which the microprocessor may be provided in some cases. Further, an LSI for data transmission, which has recently been put to practical use, may be combined with the microprocessor to simplify the software of the microprocessor. For such combination, a microprocessor Intel 8049 and a data transmission LSI Intel 8251 can be used.

Figure 2:
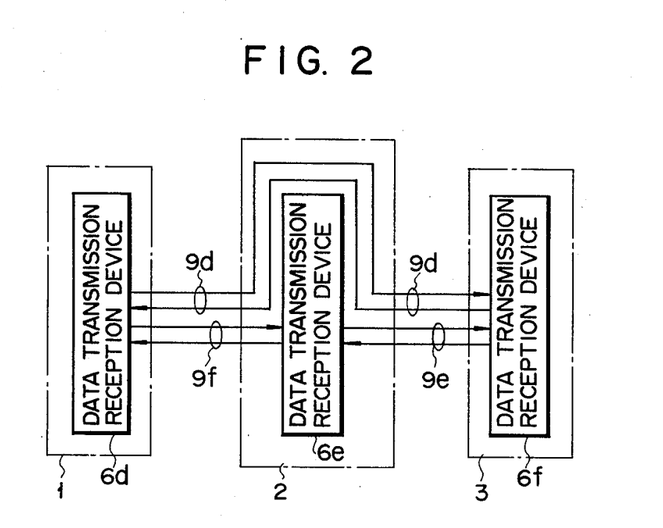
FIG. 2 is a block circuit diagram of a data transmission system for an endoscope apparatus according to another embodiment using duplex channels.

The half-duplex channels used in the aforesaid embodiment may be replaced with full-duplex channels, as shown in FIG. 2. In FIG. 2, full-duplex channels 9d, 9e and 9f are provided between a photographic attachment 1, and endoscope 2, and a light source unit 3. The use of these full-duplex channels enables simultaneous transmission and reception of data, that is, high-speed data transmission. Although the photograhic attachment 1, endoscope 2 and light source unit 3 are all coupled by means of the duplex data channels in the embodiments of FIGS. 1 and 2, this invention is not limited to such configuration. The endoscope system of the invention can be further diversified in function as compared with the function of the prior art endoscope system as long as data transmission/reception devices are provided in at least two of those three units, and a duplex data channel is provided between these two units. With the construction as shown in FIG. 1, however, if the duplex data channel 9a is cut, the data transmission/reception device 6b in the endoscope 2 will be used as a relay, and the data to be transmitted originally by means of the duplex data channel 9a will be detoured via the duplex data channel 9c, endoscope data transmission/reception device 6b, and duplex data channel 9b. Thus, the influence of the trouble in the duplex data channel 9a will be minimized to ensure safety. To reduce the duplex data channels in number, the duplex data channel 9a can be omitted so that data may be transmitted between the photographic attachment data transmission/reception device 6a and the light source unit data transmission/reception device 6c in the aforesaid manner.

Referring now to the drawings of FIGS. 3a to 3c, there will be described a specific arrangement of the data transmission system using the full-duplex channels.

Figure 3A:
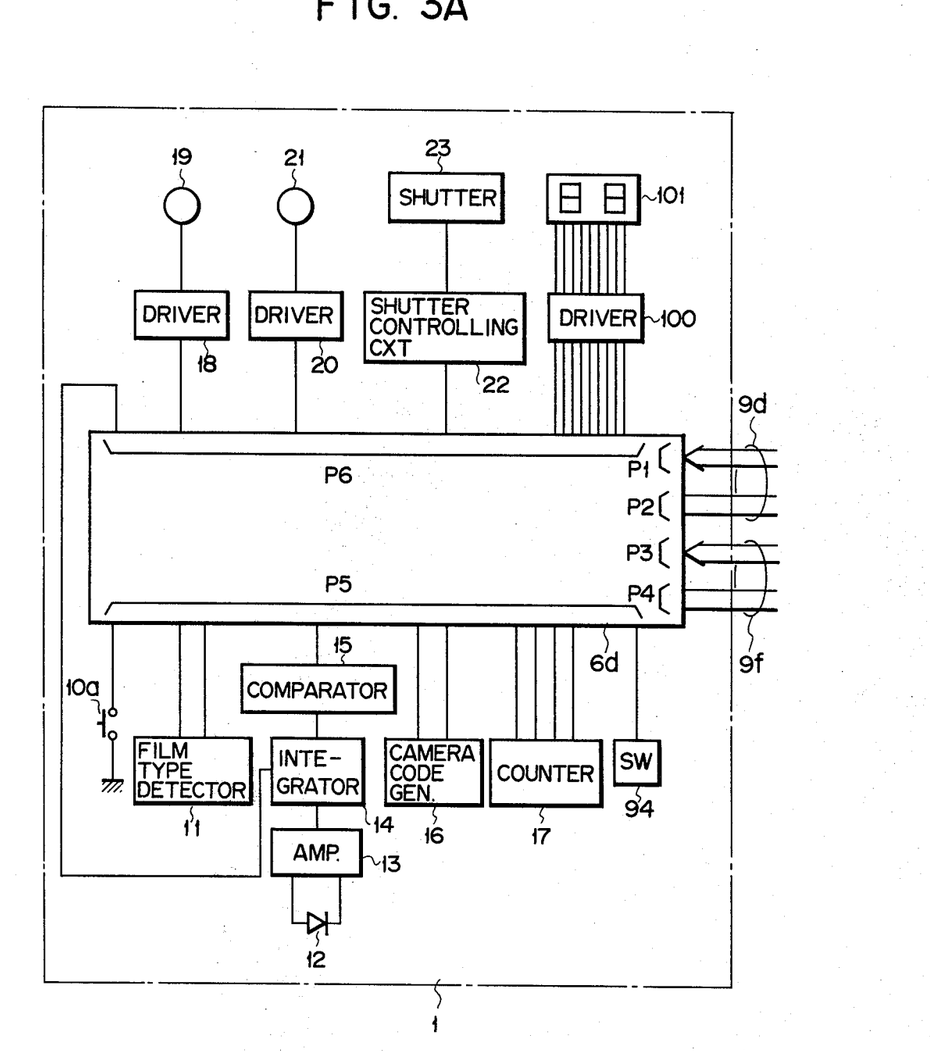
FIGS. 3A to 3C are block diagrams of a photographic attachment, an endoscope, and a light source unit of the data transmission system of FIG. 2, respectively.

As shown in FIG. 3A, the photographic attachment 1 is provided with a release switch 10a which is connected with an input port P5 of a data transmission/reception device 6d. Also, the data transmission/reception device 6d is connected with a film type detector 11 to detect film type codes corresponding to film types marked on film patrones or film cassettes. The film types include a tungsten-balanced type, daylight type, high-speed type, and popular type. These film types have their own codes which are applied to the input of the detector by means of e.g. keys for the identification of the film types. A light receiving element 12 receives part of incident light split by a half mirror disposed on the optical path of the film and an objective, and produces a photoelectric signal for automatic exposure. This photoelectric signal is amplified by an amplifier 13, and supplied to an integrator 14. The integrator 14 produces an electric signal corresponding to the amount of exposure on the film surface, and the electric signal is supplied to a comparator 15 to be compared with a reference signal. When the level of an integration signal reaches a given value, that is, when the amount of exposure on the film surface reaches a given value, the comparator 15 generates a pulse signal. The output of the comparator 15 is connected to the input port P5 of the data transmission/reception device 6d. The input port P5 is further connected with a camera code generator 16, a digital frame counter 17, and a shutter full-open detector 94. The camera code generator 16 produces a camera code corresponding to the model of the photographic attachment of the endoscope. Since no code is produced if no photographic attachment or camera is mounted on the endoscope, the camera code can indicate the setting of the camera. The digital frame counter 17 produces a BCD or binary code corresponding to the number of photographed or unphotographed frames.

An output port P6 of the data transmission/reception device 6d is coupled with a charging-over indicating LED 19, an automatic exposure indicating LED (Light Emitting Diode) 21, and a frame number display 101 through drivers 18, 20 and 100, respectively. Further, the output port P6 is connected with a shutter controlling circuit 22 for controlling a shutter 23.

Figure 3B:
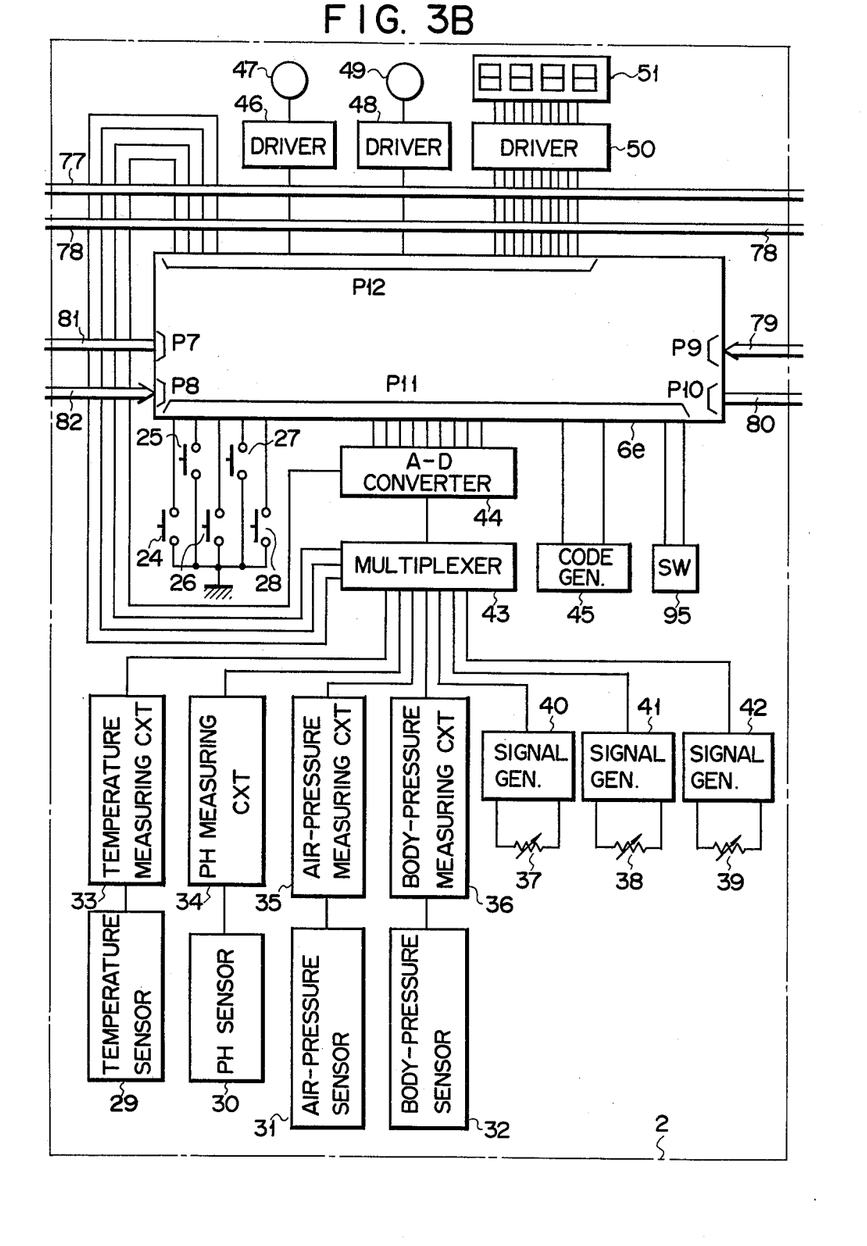

As shown in FIG. 3B, an input port P11 of a data transmission/reception device 6e of the endoscope 2 is connected with an air-feed switch 24, a water-feed switch 25, a suction switch 26, an feed-gas changing switch 27, and a filter insertion switch 28. Moreover, the input port P11 is connected with a temperature measuring circuit 33, a pH measuring circuit 34, an air-pressure measuring circuit 35, a body-pressure measuring circuit 36, an observation light quantity adjusting signal generator 40, an air-feed adjusting signal generator 41, and a feed-water pressure adjusting signal generator 42 through an A-D converter 44 and an analog signal multiplexer 43. The temperature measuring circuit 33 is connected with a temperature sensor 29 such as a thermistor for measuring the temperature inside the body cavity. The pH measuring circuit 34 is connected with pH sensor 30 which, formed of e.g. subminiature glass electrodes, is attached to the distal end of the endoscope. The air-pressure measuring circuit 35 is connected with an air-pressure sensor 31 which, formed of e.g. a semiconductor piezoelectric transducer, is attached to the distal end of the endoscope. The air-pressure measuring circuit 35 measures the air pressure inside e.g. a stomach which is expanded by air introduced thereinto. The body-pressure measuring circuit 36 is connected with a body-pressure sensor 32 which is formed of e.g. a strain gauge or semiconductor piezoelectric transducer and attached to the distal end of the endoscope. The pressure of the walls of a stomach is measured by bringing the body-pressure sensor 32 into contact with the walls. The observation light quantity adjusting signal generator 40, air-feed quantity adjusting signal generator 41, and feed-water pressure adjusting signal generator 42 are connected with an observation light quantity adjuster 37, an air-feed quantity adjuster 38, and a feed-water pressure adjuster 39, respectively. The input port P11 is further connected with an endoscope code generator 45 and a display selector switch 95. The endoscope code generator 45 produces a code determined in accordance with the type of the endoscope. An output port P12 of the data transmission/reception device 6e is connected with an air-feed control valve action indicating LED 47, a suction valve action indicating LED 49, and a digital display 51 respectively through drivers 46, 48 and 50. The digital display 51 indicates values measured by the temperature, pH air-pressure, and body-pressure measuring circuits 33 to 36. In such indication, the value to be indicated is selected by the display selector switch 95. The digital display 51 may be so constructed as to be able to exhibit the alphabet, katakana (the square form of kana, the Japanese syllabary), Chinese charcters, etc., as well as digits. Accordingly, in case of trouble in the endoscope 2 or the light source unit 3, for example, the cause of the trouble or remedy therefore may be indicated for safety. Moreover, the display 51 can be formed of an LED or LCD, and an additional display can be provided at the endoscope control section as well as in the finder.

Figure 3C:
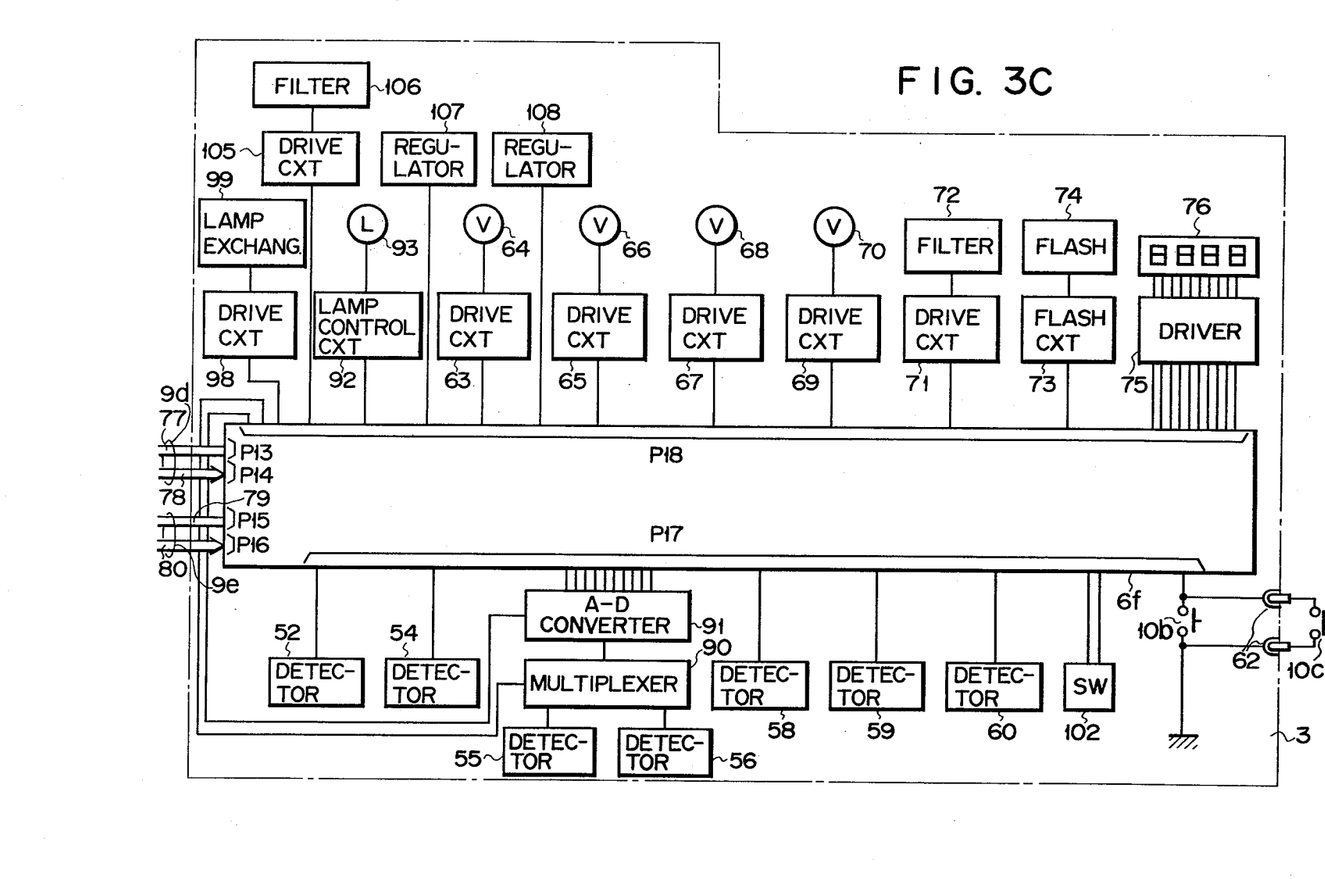

In the light source unit 3, as shown in FIG. 3C, an input port P17 is connected with an air valve action detector 52, a suction valve action detector 54, a charging-over detector 58, an automatic exposure detector 59, and an optical path switching-over detector 60. Further, the input port 17 is connected with an air-feed quantity detector 55 and a feed-water pressure detector 56 respectively through an analog signal multiplexer 90 and an A-D converter 91. The air-and water-feed control valve action detectors 52 and 54, which are to detect the actions of air-and water-feed control valves 64 and 68 connected with an output port P18 respectively through air-and water-feed control valve driving circuits 63 and 67, may be formed of circuits to detect current flowing through a solenoid operated valve or switches to be turned on in response to the mechanical actions of the valves. The air-feed quantity and feed-water pressure detectors 55 and 56, which may be formed e.g. semiconductor piezoelectric transducers, detect the quantity of airflow and the pressure of water introduced into the body cavity for each unit time, and produce analog signals corresponding to the detected air-feed quantity and feed-water pressure. One of the analog output signals from the detectors 55 and 56 is selected by a signal from the output port P18 of a data transmission-reception device 6f. The charging-over detector 58, which may be formed of e.g. a capacitor charging current detector circuit, detects that the charging of a discharge capacitor is finished with use of an electronic flash as a light source for photographing. The automatic exposure detector 59, which is to detect if the photographing is performed within the operating range of an automatic exposure circuit, that is, with a proper amount of exposure, may be formed of a circuit to detect that a commutation thyristor for turning off a main thyristor in an electronic flash control circuit 73 in the light source unit 3 is turned on. The optical path changing over detector 60, which is used where separate light sources are provided for observation and photographing, functions to ascertain if the light of an observation-light lamp 93 is off the optical path before the shutter 23 of the photographic attachment 1 is released. The detector 60 is intended to prevent the so-called fog or film exposure by observation light which will be caused if the shutter 23 is released before the light of the lamp 93 is completely removed from the optical system.

A footswitch connector 62 is a connector for connecting a release switch 10b on the panel of the light source unit 3 and a footswitch 10c in parallel with each other so that the shutter may be released when either of the switches 10b and 10c is depressed. Although the switches 10b and 10c connected to the input port P17 are connected in parallel with each other in FIG. 3C, they may be connected severally to separate terminals of the input port P17 so that they may be caused to perform substantially the same action as parallel-connected switches by means of the software for controlling the data transmission/reception device 6f. A display selector switch 102, which is intended to select the indicating information of an LED display 76 connected to the output port P18 through a driver 75, selectively leads output data from the temperature, pH, air-pressure, and body-pressure measuring circuits 33 to 36 in the endoscope 2 to the display 76. A feed-gas changing valve driving circuit 69 drives a feed-gas changing valve 70 for changing the kind of gas to be fed. A filter driving circuit 71, which may be formed of e.g. a solenoid, is provided for leading or removing a visibleray cut filter 72 to or from an optical path for illumination. The electronic flash control circuit 73, which is to control the light emission of an electronic flash 74, includes a discharge capacitor, discharge capacitor charging circuit, main thyristor for control, etc.

The LED display 76 can also indicate the number of photographed or unphotographed frames, thereby enabling an assistant operator to record findings of his partner or an endoscope operator with reference to the frame numbers of photographs. Further, the display 76 may be so designed as to be able to exhibit the alphabet and other characters, as well as digits, whereby the locations, details and remedies of an for troubles, if any, will be indicated.

An observation-light lamp control circuit 92 controls the light quantity of the observation-light lamp 93, and an optical path changing device 99 switches between the lights of the observation-light lamp and electronic flash to be led into the light guide of the endoscope. The optical path changing device 99 is driven and controlled by an optical path changing device driving circuit 98. A color temperature correcting filter 106 is controlled by a color temperature correcting filter driving circuit 105 to be inserted or removed into or from the optical systems for color temperature correction. The filter driving circuit 105 may be formed of a solenoid, for example. An air-feed quantity regulator 107 is intended to regulate the air-feed quantity per unit time, and directly controls the number of revolutions or speed of an air-feed pump. A feed-water pressure regulator 108 is intended to regulate the feed-water pressure, and directly controls the speed of a feed-water pump.

In the photographic attachment 1, endoscope 2, and light source unit 3, as described above, output ports P2 and P4 of the data transmission/reception device 6d of the attachment 1 are connected to an input port P14 of the data transmission/reception device 6f of the light source unit 3 and an input port P8 of the data transmission/reception device 6e of the endoscope 2 respectively by means of channels 78 and 82. Output ports P7 and P10 of the data transmission/reception device 6e of the endoscope 2 are connected to an input port P3 of the data transmission/reception device 6d of the photographic attachment 1 and an input port P16 of the data transmission/reception device 6f of the light source unit 3 respectively by means of channels 81 and 80. Output ports P13 and P15 of the data transmission/reception device 6f of the light source unit 3 are connected to an input port P1 of the data transmission/reception device 6d of the photograhic attachment 1 and an input port P9 of the data transmission/reception device 6e of the endoscope 2 respectively by means of channels 77 and 79. The channels 77 to 82 are one-way channels, and parts of the channels 77 and 78, 79 and 80, and 81 and 82 form the duplex channels 9d, 9e and 9f, respectively.

Now there will be described the operations of the circuits shown in FIGS. 3A to 3C. In these circuit, the data transmission/reception devices 6d, 6e and 6f severally perform polling by means of software programmed in their respective internal ROM's, thereby monitoring the states of the input ports. When several signals are received through the input ports, output data corresponding to such received signals are delivered from the data transmission/reception devices 6d, 6e and 6f through their respective output ports. An output data from one data transmission/reception device is applied to an input port of another data transmission/reception device by means of a channel. Receiving the data, each data transmission/reception device performs control of the several circuits in accordance with its own program. Several operations will be described below.

Photographic Operation

When the release switch 10a of the photograhic attachment 1 is closed, a release instruction is applied to the data transmission/reception device 6d through the input port P5. In response to this release instruction, the data transmission/reception device 6d transmits a release signal through its output port P2 to the input port P14 of the data transmission/reception device 6f of the light source unit 3 by means of the channel 78. In response to the release signal, the optical path changing device driving circuit 98 operates to drive the optical path changing device 99. The optical path changing device 99 switches the optical path from the observation light system to the photographing light system or the optical system of the electronic flash 74. When this swiching operation is completed, a detection signal is delivered from the optical path changing over detector 60, and applied to the input port P17. This detection signal is transmitted from the output port P13 to the input port P1 of the data transmission/reception device 6d of the photographic attachment 1 by means of the channel 77. In response to the detection signal, the data transmission/reception device 6d actuates the shutter control circuit 22 to release the shutter 23. At this time, an integration start signal is transmitted from the output port P6 of the data transmission/reception device 6d to the integrator 14. In response to this, the integrator 14 starts integration. When the shutter 23 opens to its full width, a shutter full-open detection signal is transmitted from the shutter full-open detector 94 through the output port P2 to the data transmission/reception device 6f by means of the channel 78. In response to this full-open detection signal, the electronic flash control circuit 73 operates to flash the electronic flash 74. The flash light reaches the distal end portion of the endoscope 2 through the light guide of the endoscope to illuminate a subject. Reflected light from the subject is formed into an image by the objective attached to the distal end of the endoscope, transmitted to the eyepiece section of the endoscope through the image guide for image transmission, and led into the photograhic attachment or camera 1 through the eyepiece section. The light introduced into the camera is split by a half mirror; most of the light reaches the film surface to expose the film, and the remaining light falls on the light receiving element 12. The output of the light receiving element 12 is converted into a voltage signal by a current-voltage converter circuit, and applied to the integrator 14. When the output of the integrator 14, i.e. a signal proportional to the amount of exposure on the film, takes a reference voltage value, that is, when the amount of exposure reaches a proper level, a pulse signal is delivered from the comparator 15, and applied to the data transmission/reception device 6d through the input port P5. This pulse signal is transmitted through the output port P2 to the input port P14 of the data transmission/reception device 6f of the light source unit 3 by means of the channel 78. In response to the pulse signal, the data transmission/reception device 6f actuates the electronic flash control circuit 73 to stop the flashing. In this case, high-speed control, as well as an improvement of exposure accuracy, can be achieved by stopping the light emission of the electronic flash 74 through interruption by means of an interruption input terminal (not shown) of the data transmission/reception device 6f without using the input port P14 of the device 6f. At the moment the light emission is stopped, the optical path changing device 99 and the shutter 23 are restored to the initial state through the output ports P6 and P18.

While the photographing has been described as being performed by operating the release switch 10a of the photogaphic attachment 1, there will now be described a case where the photographing is executed by means of the release switch 10b on the panel of the light source unit 3 or the footswitch 10c. In this case, the data transmission/reception device 6f notices that the switch 10b or 10c is turned on, and transmits a release signal to the data transmission/reception device 6d of the camera 1 by way of the channel 77. Receiving the release signal, the camera 1 performs photographing according to the same operating processes as described before. Thus, the use of the release switch 10b or footswitch 10c of the light source unit 3 enables the endoscope operator to carry out photograhing without employing his hand by ordering his assistant to release the shutter or by stamping the footswitch 10c himself. Accordingly, the operator will be able to perform the photographic operation with ease even if he is engaged in angle control for changing the direction of the distal end of the endoscope or in forceps insertion where he would have his hands full.

In taking a photograph by using the endoscope 2 and the photographic attachment 1, there will be presented the following problems, unlike the case of conventional photographing.

An image guide, which is contained in the endoscope 2 and formed of such material as optical fibers having a function to transmit an image formed at the distal end of the endoscope to the eyepiece section thereof, varies greatly in its area with the model of the endoscope 2. The photographic attachment 1 photographs the image transmitted to the end of the image guide via the eyepiece section of the endoscope 2, so that other portions than the image guide will come out dark.

Accordingly, if the light receiving element 12 contained in the photographic attachment 1 is used in the mean-photometric manner as it is called so that the automatic-exposure photographing may be performed in accordance with the output signal of the element 12, then proper exposure will not possibly be done due to the difference in the area of the image guide. Namely, if the amplifier 13, integrator 14, comparator 15, etc. are adjusted so that the proper exposure may be obtained when the area of the image guide is small, use of a large-area image guide will cause the comparator 15 to deliver a pulse signal before the proper exposure is obtained, thereby rendering an image on the film underexposed.

This invention will provide an effective measure to counter such problems provided the following is observed. An endoscope code delivered from an endoscope code generator and applied to the data transmission/reception device 6e through the input port P11 is applied through the output port P7 to the input port P3 of the data transmission/reception device 6d of the photographic attachement 1 by means of the channel 81. The data transmission/reception device 6d decodes the input endoscope code, and supplies the comparator 15 with a comparison voltage corresponding to the area of the image guide of the endoscope.

In consequence, the comparison voltage can be increased with the increase of the area of the image guide, and a pulse signal is delivered from the comparator 15 with proper exposure without regard to the area of the image guide, thereby enabling you constantly to take a proper-exposure endoscopic photograph.

Operation Based on Film Type Code

When the film type detector 11 delivers a film type code, the code signal is applied to the data transmission/reception device 6d of the photographic attachment 1, and transmitted to the data transmission/reception device 6f of the light source unit 3 by means of the channel 78. In the data transmission-reception device 6f, the film type code is identified, and a suitable color temperature conversion filter (not shown) corresponding to the film type is put into the optical path of the electronic flash 74.

Operation Based on Camera Code

A camera code generator 16 delivers a signal in accordance with the model of the camera. The camera code signal is applied to the data transmission/reception device 6d, where it is transmitted to the data transmission/reception device 6f of the light source unit 3 by means of the channel 78. When the camera code signal is received by the data transmission/reception device 6f, the photographing sequence is changed so that the optimum sequence for the camera model may be executed. For example, if it is revealed by the camera code signal that a camera without the shutter full-open detector 94 is connected to the endoscope, the photographing sequence is switched to timer-control sequence to enable operation which requires no shutter full-open detection. When it is detected that no camera is coupled with the endoscope, the photographing sequence will not be operated if the release switch 10b and footswitch 10c are depressed. Thus, waste of power consumption such as wasteful flashing of the electronic flash 74 will be prevented.

Operation of Digital Frame Number Counter

The digital frame number counter 17 digitally counts the number of releases, frequency of film winding, etc., and a count value is applied to the data transmission/reception device 6d through the input port P5. The data transmission/reception device 6d supplies the count data to the frame number display 101 via the output port P6 and the driver 100 to cause the display 101 to indicate the frame number. At the same time, the count data is transmitted to the data transmission/reception device 6f of the light source unit 3 via the output port P2, channel 78, and input port P14. At this time, the display selector switch 102 is so set as to cause the display 76 to indicate the frame number. Thus, whereas the prior art system allows only the chief operator to watch the frame number, the system of this invention allows also the assistant operator to watch the display of the light source unit to know the frame number. Accordingly, the assistant operator can enter in clinical charts findings or regions specified by the chief operator in response to the frame number or keep a recording corresponding to the frame number while watching a lecturescope.

Operations for Air Feed, Water Feed, and Suction

The operating state of the air-feed switch 24 is identified by the data transmission/reception device 6e through the input port P11, and a state signal is transmitted to the data transmission/reception device 6f of the light source unit through the output port P10, channel 80, and input port 16. The transmission/reception device 6f drives the driving circuit 63 in accordance with the operating state of th air-feed switch 24, thereby opening or closing the air-feed control valve 64. Likewise, the water-feed control valve driving circuit 67 and a suction valve driving circuit (not shown) are operated in accordance with the operating states of the water-feed switch 25 and the suction switch 26. In response to the actions of the driving circuit 67 and the suction valve driving circuit, the water-feed control valve 68 and a suction valve (not shown) are operated or controlled, respectively. In such valve control, fine adjustments of air feed, water feed and suction can be performed to facilitate endoscopy by transmitting digital signals corresponding to the strokes at which the switches are depressed so that the opening of each valve may be set in stages, as well as simple on-off operations of the switches. Feed-gas Changing Operation Data for the operating state of the feed-gas changing switch 27 is transmitted to the data transmission/reception device 6f of the light source unit 3 in the same manner as the state of the air-feed switch 24. Receiving the state data, the data transmission/reception device 6f drives the feed-gas changing valve driving circuit 29 to control the feed-gas changing valve 70 for the change of feed-gas. For the feed-gas, there may be used gas mixtures of air and carbonic acid gas, air and laughing gas, etc., or a combination of three or more gases. In this case, the feed-gas changing switch 27 need have an output terminal of two bits or more. A cylinder or carbonic acid gas or laughing gas may be disposed in-or outside the light source unit 3.

Filter Insertion

Data for the operating state of the filter insertion switch 28 is transmitted to the data transmission/reception device 6f in the same manner as the state of the air-feed switch 24. In response to the transmitted data, the transmission/reception device 6f drives the filter driving circuit 71 including a solenoid to set the visible-ray cut filter 72 in the optical path of the illumination light. The filter used in this case is a filter which may be used for fluorescent observation of the stomach combining fluorescent dyes with ultraviolet rays. Namely, when using a light source lamp such as a mercury lamp that emits both visible rays and ultraviolet rays, the ultraviolet rays only are passed through the filter to allow only the fluorescent dyes to be observed. When the filter insertion switch 28 is not depressed, the visible-ray cut filter 72 is removed from the optical path, and observation is conducted with use of common visible rays.

Temperature, pH, Air-pressure, and Body-pressure Detection

A temperature signal corresponding to a temperature detected by the temperature sensor 29 is delivered from the temperature measuring circuit 33. Likewise, pH, air-pressure and body-pressure detected by the pH sensor 30, air-pressure sensor 31, and body-pressure sensor 32 delivered as pH, air-pressure, and body-pressure signals from the pH measuring circuit 34, air-pressure measuring circuit 35, and body-pressure measuring circuit 36, respectively. These signals, together with the output signals of the observation light quantity adjusting signal generator 40, air-feed quantity adjusting signal generator 41, and feed-water pressure adjusting signal generator 42, are applied to the analog signal multiplexer 43. The multiplexer 43 applies to the A-D converter an analog signal designated by an input designating digital signal from the data transmission/reception device 6e. The A-D converter 44 converts its input signal into a digital signal, and applies it to the data transmission/reception device 6e. This digital signal is indicated on the digital display 51, and also is transmitted to the data transmission/reception device 6f of the light source unit 3 by means of the channel 80 and indicated on the display 76. The data to be indicated can be designated by the display selector switches 95 and 102.

Also, the digital signal applied to the data transmission/reception device 6e can be transmitted to the transmission/reception device 6d of the photographic attachment 1 by means of the channel 81 so as to be indicated on the frame number display 101. In this case, the display selector switch 95 may be used for the selection of the data to be indicated. The use of the switch 95 for this purpose, however, is not very advisable because it is remote from the release switch 10a. In order to eliminate such awkwardness, it is necessary only that a switch (not shown) having the same function with the display selector switch 95 be provided in the photographic attachment 1 and connected to the input port P5 of the data transmission/reception device 6d so that a selection signal may be transmitted to the data transmission/reception device 6e of the endoscope 2 by means of the channel 82. The use of the two display selector switches will present no problems if the signal from the display selector switch 95 is prohibited from being received by the data transmission/reception device 6e. It may be possible, moreover, to provide data superimposing means (not shown) in the photographic attachment 1 to superimpose those data including the temperature, pH, air-pressure, and body-pressure over the film in photographing the subject.

Observation Light Quantity Regulation, Air-feed Quantity Regulation, and Feed-water Pressure Regulation Electric signals corresponding to the regulation values of the observation light quantity adjuster 37, air-feed quantity adjuster 38, and feed-water pressure adjuster 39 are delivered respectively from the observation light quantity adjusting signal generator 40, air-feed quantity adjusting signal generator 41, and feed-water pressure adjusting signal generator 42, and applied to the analog signal multiplexer 43. The multiplexer 43 is supplied with the input designating digital signal from the data transmission/reception device 6e, and one of the output signals from the measuring circuits 33 to 36 and the adjusting signal generators 40 to 42 is selected. The output signal from the multiplexer 43 is applied to the A-D converter 44 to be converted into a digital signal, and transmitted by the data transmission/reception device 6e to the data transmission/reception device 6f of the light source unit by means of the channel 80. Receiving the data, the data transmission/reception device 6f drives the observation-light lamp control circuit 92, air-feed quantity regulator 107, and feed-water pressure regulator 108 in accordance with the data, thereby controlling the observation light quantity and the air-feed quantity and feed-water pressure per unit time.

Operation Based on Endoscope Code

The endoscope code generator 45 produces codes corresponding to the types of endoscope. For example, a fiberscope for stomach examination is represented by a code 01; coeloscope by 10 and fiberscope for colon examination by 11. The use of the endoscope codes is particularly effective where the spectral properties of the optical systems of the several endoscopes vary greatly. If the spectral properties of the optical systems are different, the observed colors or picture colors will vary with the types of the endoscopes although with use of the same light-source lamp, and it will be very hard to improve the color reproducibility for all these endoscopes. In such case, when the code signal from the endoscope code generator 45 is transmitted to the data transmission/reception device 6f of the light source unit 3 by means of the channel 80, the color temperature correcting filter 106 is set in the optical path in response to the endoscope code so that observation and photographing may be performed in accordance with the spectral property of the endoscope used to provide the optimum color reproduction at all times.

Detection of Actions of Air-feed Control Valve and Suction Valve

The air-feed control valve action detector 52 detects the action of the air-feed control valve 64. A detection signal from the detector 52 is transmitted to the data transmission/reception device 6e of the endoscope 2 by means of the channel 79. In the endoscope 2, the air-feed control valve action indicating LED 47 glows to indicate the action of the air-feed control valve 64 in response to the detection signal. This indication can be recognized within the finder of the endoscope 2. Capable of ascertaining if the air-feed control valve 64 in the light source unit 3 operates securely when the air-feed switch 24 is operated while looking in the finder, the endoscope operator may immediately notice any trouble that the air feed cannot be stopped due to a failure of the air-feed control valve 64, thereby quickly taking necessary measures for the safety of his patient, such as removal of the endoscope from the patient body and depression of the suction switch 26 for aspiration. For the suction valve action detector 54, the suction valve action indicating LED 49 glows for the indication of the action of the suction valve in just the same manner as aforesaid.

Detection of Air-feed Quantity and Feed-water Pressure

The air-feed quantity detector 55 produces an output signal corresponding to the air-feed quantity per unit time, which is applied to the analog signal multiplexer 90. The feed-water pressure detector 56 delivers an electric signal corresponding to the feed-water pressure, which is also applied to the analog signal multiplexer 90. The multiplexer 90 is supplied with an input designation signal from the data transmission/reception device 6f, and either the air-feed quantity signal or the feed-water pressure signal is selected by the designation signal. The signal transmitted through the multiplexer 90 is converted into a digital signal by the A-D converter 91 and indicated on the display 76, and further transmitted to the data transmission/reception device 6e of the endoscope 2 by means of the channel 79. In the endoscope 2, the received air-feed quantity or feed-water pressure data is indicated on the digital display 51. The display information is selected by the display selector switches 102 and 95.

Charging Over Detection

The charging over detector 58 detects the charging state of a main charging capacitor for electric charges to flash the electronic flash 74. A detection signal from the detector 58 is transmitted to the data transmission/reception device 6d of the photographic attachment 1 by means of the channel 77. In the photographic attachment 1, the charging over indicating LED 19 glows to indicate "charging over" in response to the charging over detection signal. Thus, the endoscope operator may ascertain if the flash photographing is possible.

Automatic Exposure Detection

The automatic exposure detector 59 is intended to detect if the so-called auto-flash photographing is performed properly. When the detector 59 detects an automatic exposure action, a detection signal from the detector 59 is transmitted to the data transmission/reception device 6d of the photographic attachment 1 by means of the channel 77. In the photographic attachment 1, the automatic exposure indicating LED 21 glows to indicate "proper automatic-exposure photographing" in response to the detection signal.

Figure 4:
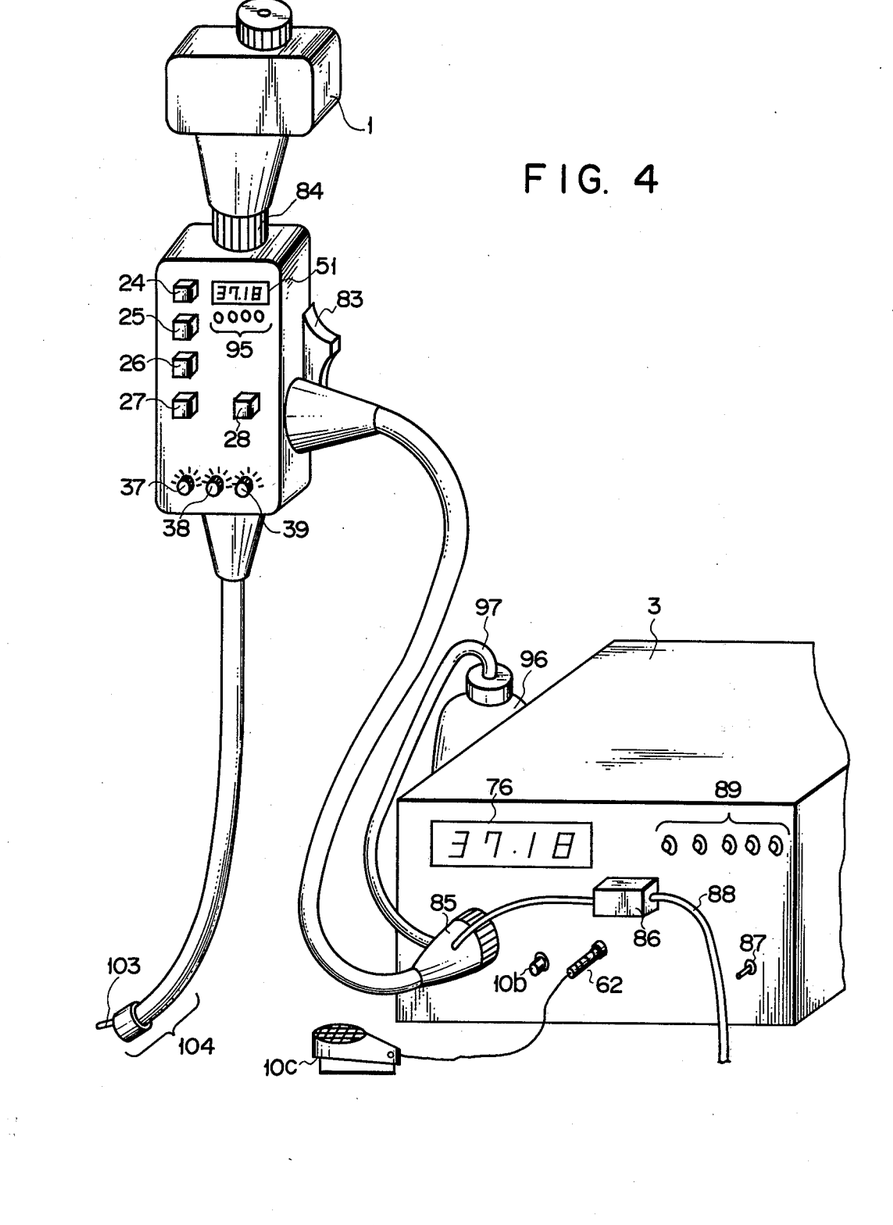
FIG. 4 is a perspective view of an endoscope system using the data transmission system of the invention.

FIG. 4 shows an endoscope system using the data transmission system of this invention. In FIG. 4, the photographic attachment 1 can be attached and detached to and from the eyepiece section of the endoscope 2. Instruction signals are transmitted to the light source unit 3 by depressing the air-feed switch 24, water-feed switch 25, suction switch 26, feed-gas changing switch 27, and filter insertion switch 28, and the valves and solenoids go into action in response to the several instructions. The observation light quantity, air-feed quantity, and feed-water pressure can be adjusted by means of the adjusters 37, 38 and 39, respectively. The temperature, pH, air-pressure, and body-pressure sensors are incorporated in a sensor section 103. The sensor section 103 may incorporate all or some of these sensors. Alternatively, the sensor section 103 may be so designed that necessary sensors can be removably attached to the sensor section 103 by means of a socket structure.

The photographic attachment or camera can be remotely released by depressing the release switch 10b or the footswitch 10c. The footswitch 10c is connected to the light source unit 3 by means of the connector 62. An angle control knob 83 is provided for changing the direction of a distal end portion 104 of the endoscope 2. The endoscope 2 is connected to the light source unit 3 by means of a scope connector 85. A suction valve unit 86 contains therein the suction valve to be operated by the suction switch 26, and is so designed as to be able to be attached to and detached from the light source unit 3 for the ease of cleaning and disinfection. The suction valve unit 86 is coupled with an external aspirator by means of a suction tube 88.

The light source unit 3 is connected to power supply by turning on a main power switch 87. The display 76 indicates the number of photographed or unphotographed frames, temperature, pH, air-pressure, body-pressure, etc. The display information of the display 76 is selected by means of display selector switches 89. A feed-water bottle 96 contains distilled water for feed water. The distilled water in the feed-water bottle 96 is led to the scope connector 85 by means of a water-feed tube 97, and transferred to the distal end portion 104 of the endoscope. Like the display 76 of the light source unit, the digital display 51 of the endoscope indicates the number of frames, temperature, pH, air-pressure, body-pressure, etc. The display information is selected by means of display selector switches 95. The display selector switches 95 can select the information independently of the display selector switches 89 of the light source unit.

According to the data transmission system of this invention as described above, data transmission/reception devices are disposed severally in a photographic attachment, an endoscope, and a light source unit, and duplex data channels are provided between the data transmission/reception devices, so that the data amount can be increased to diversify the function of an endoscope system used therewith. For example, any other person than an endoscope operator may release the photographic attachment or enter the operator's findings in clinical charts with reference to the number of frames, so that the operator will be able to be released from the troublesome recording work and devoted entirely to diagnosis. Moreover, since the temperature, humidity, pH, etc. can be measured by various sensors at the distal end of the endoscope, and the measured values are indicated within the finder and at the control section of the endoscope, as well as on the panel of the light source unit, so various physiological measurements on a living body, as well as endoscopic morphological observation, can be made to increase the information for diagnosis.

Figure 5A:
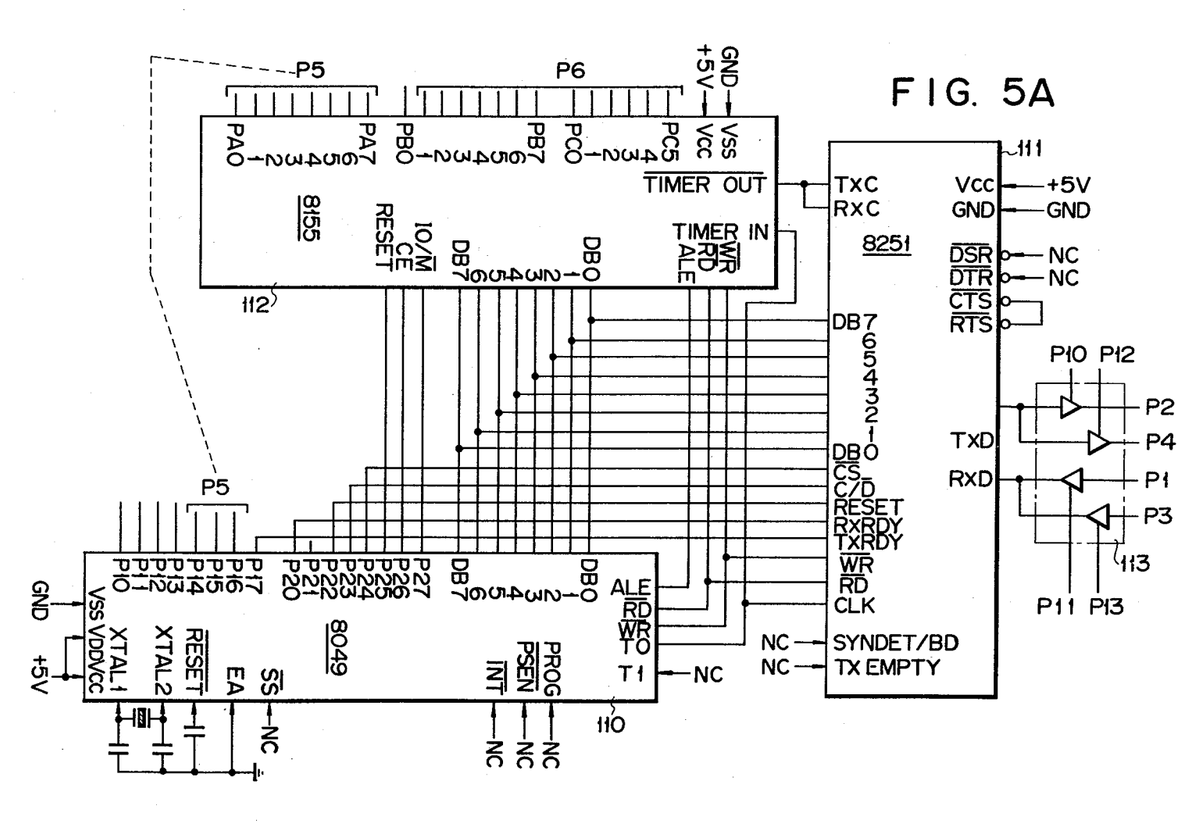
FIGS. 5A to 5C are circuit diagrams of the data transmission devices shown in FIGS. 3A to 3C, respectively.
Figure 5B:
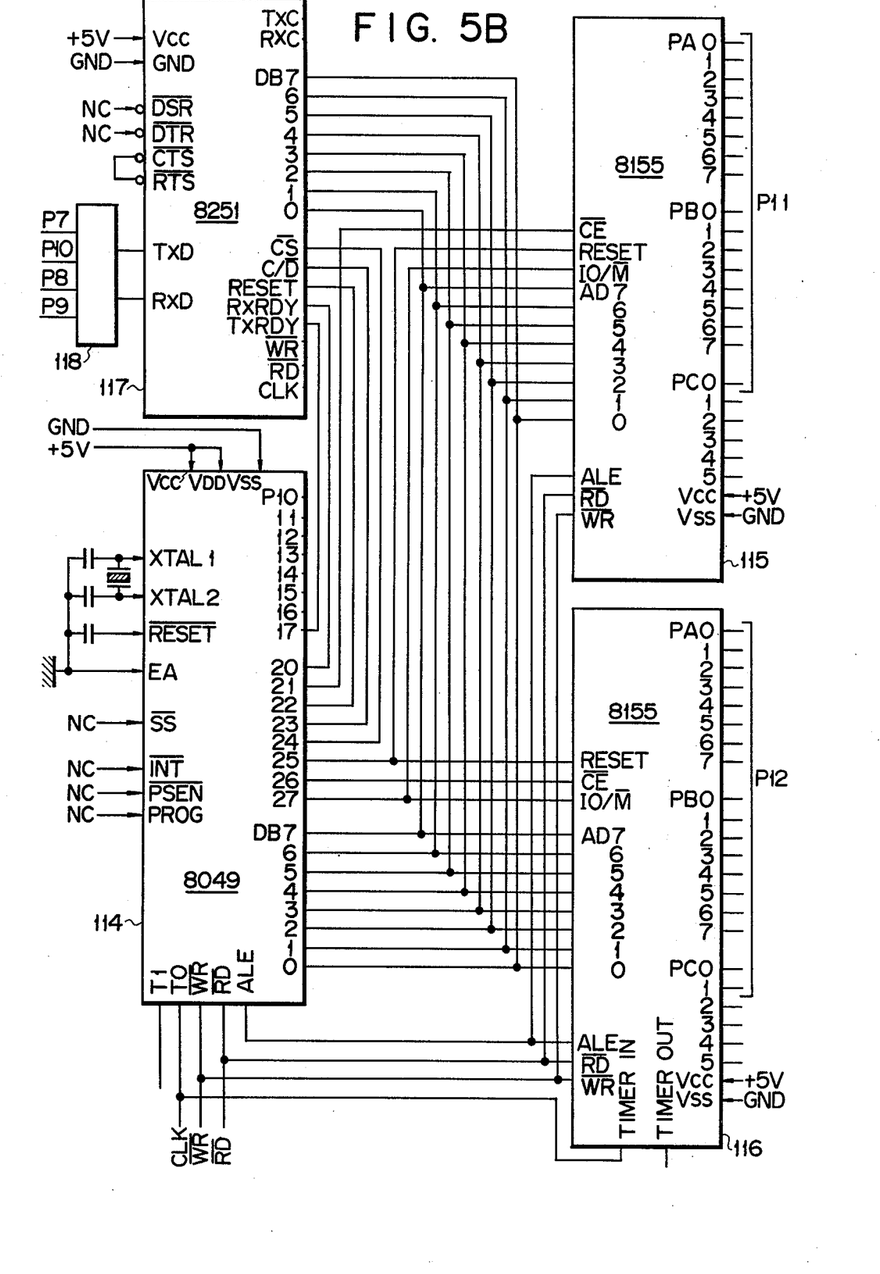
Figure 5C:
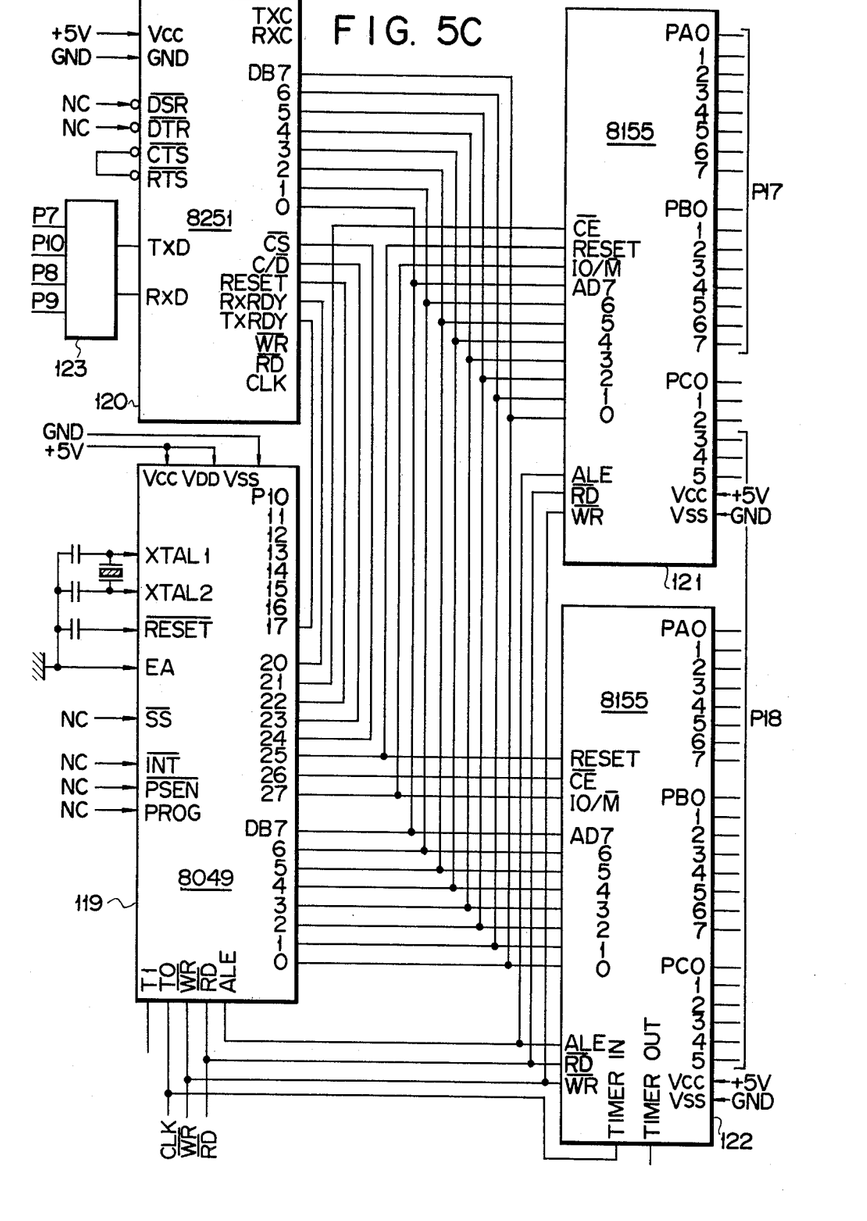

The data transmission/reception devices 6d, 6e and 6f are constructed as shown in FIGS. 5A to 5C, respectively. As shown in FIG. 5A, the data transmission/reception device 6d is composed of a microcomputer (e.g., Intel 8049) 110, a universal synchronous-asynchronous transmitter-receiver (USART) (e.g., Intel 8251) 111, a controller (e.g., Intel 8155) 112 and a logic circuit (SN74LS126A) 113. Likewise, as shown in FIG. 5B, the data transmission/reception device 6e is composed of a microcomputer (e.g., Intel 8049) 114, controllers (e.g., Intel 8155) 115, 116, a USART (e.g., Intel 8251) 117, and a logic circuit (SN74LS126A) 118. As shown in FIG. 5C, moreover, the data transmission/reception device 6f is composed of a microcomputer (e.g., Intel 8049) 119, a USART (e.g., Intel 8251) 120, controllers (e.g., Intel 8155) 121, 122, and a logic circuit (SN74LS126A) 123.

What is claimed is:

1. A data transmission system for an endoscope apparatus which performs data-transmission between at least two of an endoscope, a photographic attachment and a light source unit, comprising:
    a first data transmission/reception device provided in the light source unit and including at least one data generating means and at least one means responding to a reception data;
    a second data transmission/reception device provided in at least one of the endoscope and the photographic attachment;
    two-way data transmission lines provided in the endoscope to relay data between the first and second data transmission/reception devices; and
    means for connecting the data transmission/reception devices and the two-way data transmission lines.

2. A data transmission system according to claim 1, wherein the first data transmission/reception device is connected to the two-way data transmission lines of the endoscope by coupling a connector of the endoscope to the light source unit.

3. A data transmission system according to claim 1 or 2, wherein the second data transmission/reception device is provided in the endoscope and connected to the two-way data transmission lines.

4. A data transmission system according to claim 1 or 2, wherein the second data transmission/reception device is provided in the photographic attachment and is connected in the two-way data transmission lines by mounting the photographic attachment on the endoscope.

5. A data transmission system according to claim 1 or 2, wherein each of the endoscope and the photographic attachment is provided with a second data transmission/reception device which is connected to the two-way data transmission lines.

6. A data transmission system for an endoscope apparatus according to claim 1 wherein said data transmission/reception device provided in said photographic attachment includes an input port connected to release switch, a film type detector for detecting a film type code, an exposure calculator for calculating an exposure amount of a film, a counter for counting frames of the film, and a shutter-full-open detector for detecting a full-open of the shutter, and an output port connected to an auto-exposure display and a display for displaying the number of frames of the film.

7. A data transmission system for an endoscope apparatus according to claim 1 or 6 wherein said data transmission/reception device of said endoscope includes an output port connected to an air-feed control valve action indicating means, a suction valve action indicating means, and a display for displaying at least measured values.

8. A data transmission system for an endoscope apparatus according to claim 1 wherein said data transmission/reception device provided in said endoscope includes an input port connected to an air-feed switch, a water-feed switch, a suction switch, a feed-gas changing switch, and a filter insertion switch, an input port connected to a temperature measuring circuit, a pH measuring circuit, air-pressure measuring circuit, and a body-pressure measuring circuit; and an input port connected to an observation light quantity adjusting signal generator, an air-feed quantity adjusting signal generator and a feed-water pressure adjusting signal generator.

9. A data transmission system for an endoscope apparatus according to claim 1 wherein said data transmission/reception device of said light source unit includes an input port connected to an air valve action detector, a suction valve action detector, a charging-over detector, an automatic exposure detector, and an optical path switching-over detector.

10. A data transmission system for an endoscope apparatus according to claim 1 or 9 wherein said data transmission/reception device of said light source unit includes an output port connected to an electronic flash, a filter driving circuit, an air-feed valve device, a water-feed valve device, a suction valve device, an observation light source circuit and a display.

* * * * *